United States Patent [19]

Bell et al.

[11] Patent Number: Plant 7,490

[45] Date of Patent: Apr. 9, 1991

[54] MACADAMIA NAMED "HIDDEN VALLEY A4"

[76] Inventors: Henry F. D. Bell; Margaret A. Bell; David J. D. Bell, all of Box 6, Beerwah, Queensland 4519, Australia

[21] Appl. No.: 344,279

[22] Filed: Apr. 26, 1989

[30] Foreign Application Priority Data

Apr. 26, 1988 [AU] Australia ..... 88/001

[51] Int. Cl.[5] ..... A01H 5/00

[52] U.S. Cl. ..... Plt./30

[58] Field of Search ..... Plt. 30

*Primary Examiner*—Howard J. Locker

*Attorney, Agent, or Firm*—Quarles & Brady

[57] ABSTRACT

A new variety of Macadamia hybrid *Integrifolia*×*tetraphylla* has been identified that is particularly characterized by its high number of serrations per unit length on its leaf edge and a ratio of 1:1 between 3-leaf and 4-leaf whorls.

3 Drawing Sheets

The present invention is directed to a new and distinct variety of Macadamia tree believed to be a cross of *Macadamia integrifolia*×*tetraphylla* which was identified in a cultivated area.

Among the distinct characteristics of this tree is a combination of an increase in leaf serrations per unit distance and a ratio of 1:1 between 3-leaf and 4-leaf whorls as sampled over a sample of a minimum 100 specimens.

Asexual reproduction of the new variety has been accomplished by grafting scion stock taken from the original seedling plant onto both seedling and mature rootstock of various other Macadamia varieties. The variety has maintained character regardless of rootstock, and exhibitied the following characteristics and distinctions true to form through succeeding propagations.

Figure 1:
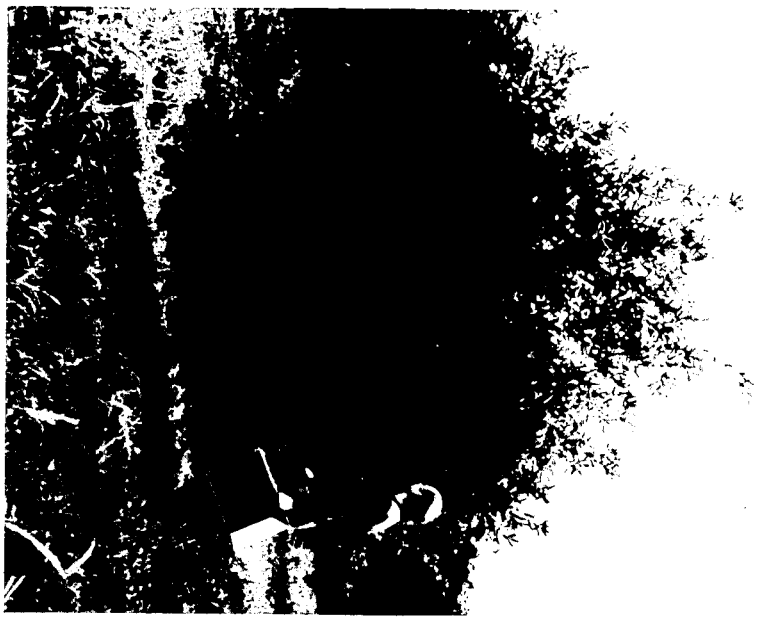
FIG. 1 shows a typical tree specimen of the new variety, named "Hidden Valley A4".
Figure 2:
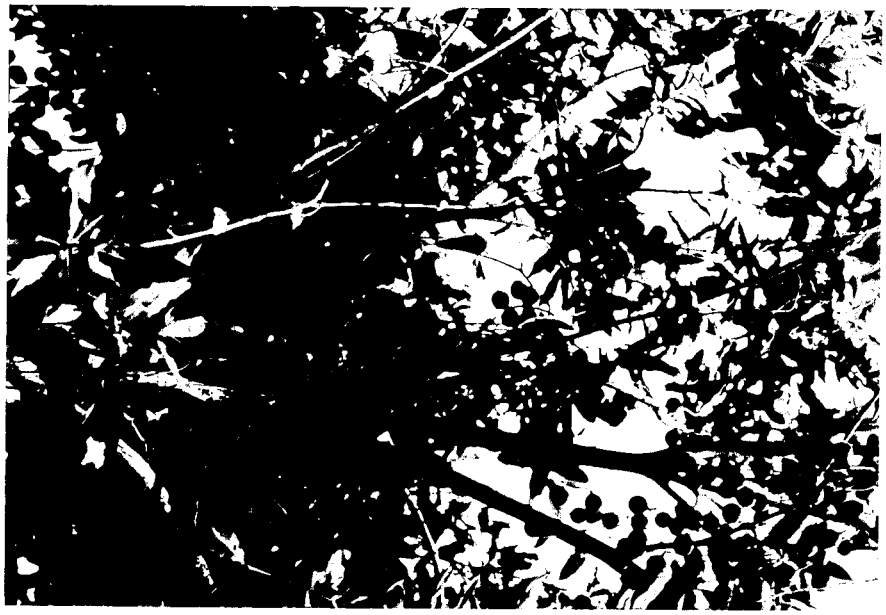
FIG. 2 shows typical nut clusters of the new variety.
Figure 3:
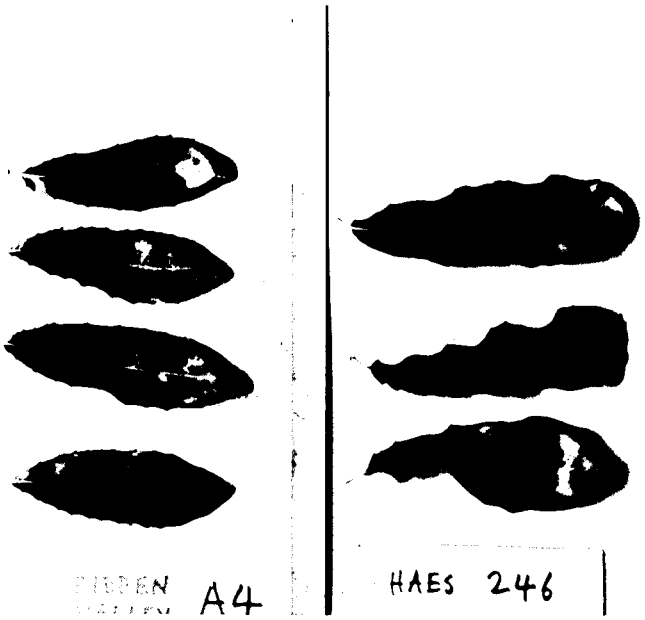
FIG. 3 shows a comparison of the leaves of the new variety with those of the known variety 'HAES 246'.
Figure 4:
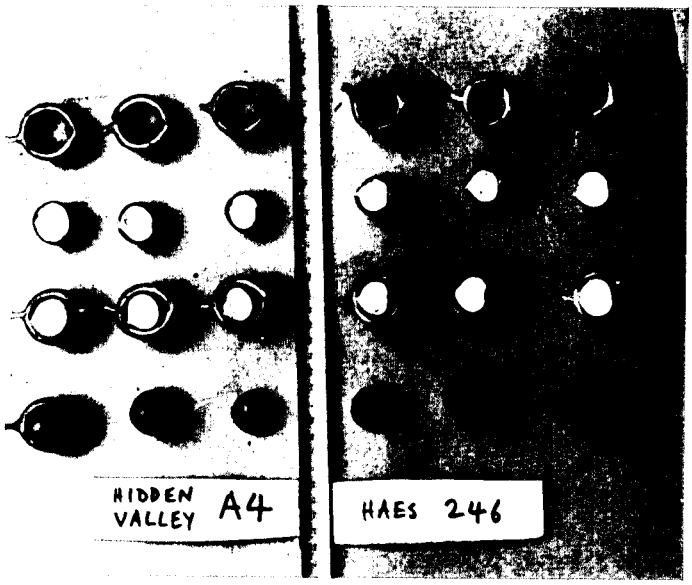
FIG. 4 shows a comparison of the kernel and nut of the new variety with the kernal and nut of the known variety 'HAES 246'.
Figure 5:
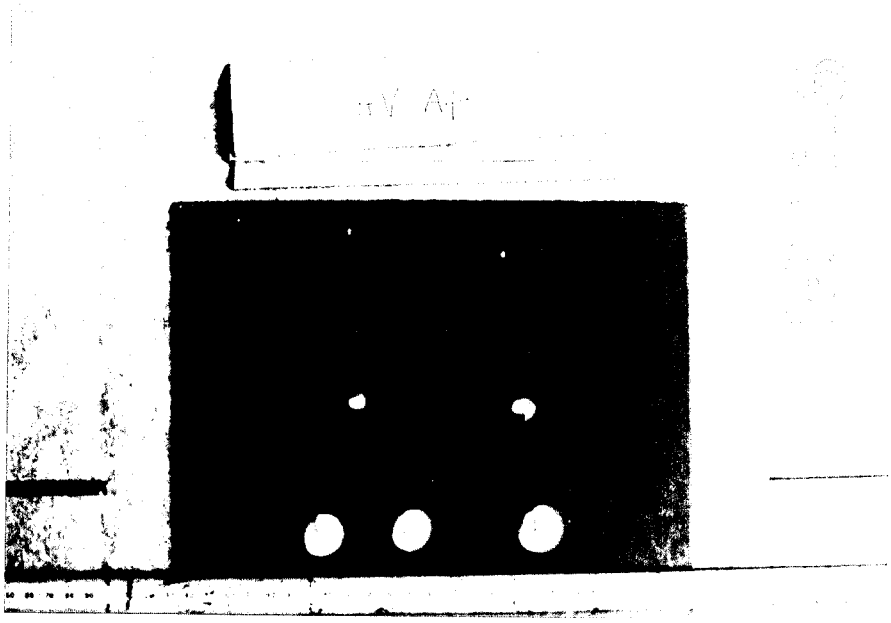
FIG. 5 shows an enlarged view of the kernel and nut of the new variety.

The variety results from a seedling derived from the open pollination of a female parent of the variety Renown, itself a hybrid of *M. integrifolia*×*M. tetraphylla*. The seedling may have arisen from self-pollination or from cross-pollination with the nearest possible pollinators being of the varieties Own Choice, Keauhou, Kakea and N.R.G. Based on morphological comparison, the most likely pollen parent is Own Choice. The cultivar has been successfully and successively grafted onto a variety of rootstock yielding trees of consistent character and having good yield characteristics, while maintaining kernel quality and beneficial growth characteristics. The cultivar was discovered and propagated at Hidden Valley Plantations, Beerwah, Queensland, Australia.

The following is a detailed description of the new variety, with color terminology determined in accordance with The Royal Horticultural Society (R.H.S.)

Colour Chart number. The characteristics and morphology listed below represents mean measurements from a minimum of one hundred specimens from trees grown in Beerwah, Queensland, Australia.

Tree: The tree is semi-erect in habit (more than Keauhou but less than Nutty Glen), moderately branched with a canopy of medium density (more dense than Hidden Valley A16 but less dense than Keauhou or Own Choice). The branches are more drooping than Keauhou. Leaves are found with both three and four leaves per node in a 1:1 ratio throughout the tree, unlike Keauhou and Kau which have predominantly three leaves per node and Renown which has predominantly four leaves per node. The grafted stock is strongly vigorous with shoots of medium thickness (thinner than Own Choice but thicker than Hidden Valley A16) with a mean of 42 mm between nodes, which sparse pubescence and weak anthocyanin coloration (R.H.S. color 152A) on new flushes. The tree has a relatively short juvenile phase (shorter than Keauhou or Kau) and a higher tolerance to Cercospora husk spot than observed for Own Choice.

Leaves: The leaves are narrow elliptical with a mean 3.69 times longer than wide, broader than Nutty Glen or Renown but narrower than Keauhou or Kau with an acutely pointed tip similar to Renown. The leaves are serrate with a mean 1.36 spines per cm which is characteristic and more than any known variety. Serrations are more shallow than Nutty Glen and spines are shorter than Renown. Leaves are only weakly undulated and weakly rolled compared with Keauhou. The young leaves are pale green (R.H.S. 137B) and mature leaves are dark green (R.H.S. 139A) and dull surfaced (similar to Nutty Glen) with distinctly lighter margins (R.H.S. 10A).

*Mean leaf length.*—144.54 mm with standard deviation (s.d.) of 22.6.

*Mean leaf width.*—39.23 mm with s.d. of 5.84.

*Mean petiole length.*—8.3 mm with s.d. of 1.48.

Flower: The racemes are cream colored, larger than Keauhou or Kau, and very dense on the tree. The tree has a shorter flowering period than Keauhou, which starts earlier and finishes later, but a longer flowering period than Hidden Valley A16. The tree has a tendency to have a second late flowering in seasons with favorable rainfall.

Fruit: The husk is of medium thickness (similar to Keauhou, thinner than Renown) with a medium hilum end point (smaller than Renown and larger than Kau) and a mildly shouldered pedicel (less than Own Choice). Husk dehiscence is partly on the tree (less than Nutty Glen and Renown) but mainly on the ground. There is an average of 1.7 nuts per raceme. There is no pre-germination on the tree observed (as in Nutty Glen) and very low incidence of fruit remaining on the tree or double embryo fruit as compared with Own Choice.

*Mean fruit length.*—50.05 mm with s.d. 2.82 (with pedicel and hilum).

*Mean fruit width.*—33.76 mm with s.d. 1.76.

Nut: The nuts are oval, 1.04 times longer than wider, less oval and more even than Renown but less round than Keauhou. The shell is light brown (R.H.S. 164A) with a smooth surface (smoother than Nutty Glen or Renown but more coarse than Kau) and a moderate sheen (more than Nutty Glen but less than Keauhou). The shell is thinner at the micropyle end (thinner than Kau but thicker than Nutty Glen). The suture is about the same color as the shell while the micropyle is barely visible. No twin mark is evident. There is moderate (less than Renown or Nutty Glen) pale flecking (R.H.S. 165C) in radial streaks from the micropyle end.

*Mean nut diameter.*—26.27 mm (Range 22–30 mm) with s.d. 1.38.

*Mean nut weight.*—7.5 gm.

Kernel: The kernel is ovoid, creamy white with very little upper/lower color difference and a mean weight of 3.5 gm. The kernel averages about 45% of the weight of the nut at 1.5% moisture content. All kernels have an oil accumulation about above 72% (100% first grade floaters recorded).

Yield: Recorded nut yields to date have been estimated to be higher per unit area than for Keauhou or Own Choice. This is based on recording yield per tree divided by tree silhouette area.

The following Table 1 compares many of these features of Hidden Valley A4 (HVA4) with the other varieties Hidden Valley A16 (HVA16), Keauhou, Kau, Own Choice, Nutty Glen, and Renown.

TABLE 1

| Character | HV A4 | Keauhou | Kau | Own Choice | Nutty Glen | Renown |
|---|---|---|---|---|---|---|
| | | | TREE | | | |
| Growth habit | semi-erect | spreading | erect | spreading | semi-erect | semi-erect |
| Canopy density | medium low | medium | high | high | low | medium |
| Lower branch attitude | drooping | level | strongly rising | drooping | rising | drooping |
| Vigour, grafts | v-strong | medium | med-weak | strong | | strong |
| Shoot thickness | medium | medium | med-thin | thin | med-thin | medium |
| Anthocyanin colouration | weak RHS 152A | absent | absent | weak | | medium weak |
| Juvenile phase | v-short | medium | long | med-short | | |
| tc,1 LEAF | | | | | | |
| No. per axis | 3,4 (50%) | 3 | 3 | 3 | 4 | 4 |
| Shape | Narrow Elliptical | Obovate | Obovate | Narrow Elliptical | Narrow Obovate | Broad Lanceolate |
| Tip | acute pointed | obtuse rounded | obtuse pointed | obtuse rounded | acute either | acute pointed |
| Length/breadth | 3.69 | 3.25 | 3.42 | 2.81 | 4.53 | 3.91 |
| length (mm) | 144.54 | 138.82 | 125.09 | 128.16 | 153.40 | 169.93 |
| Petiole length (mm) | 8.28 | 10.43 | 9.24 | 8.65 | 4.77 | 7.33 |
| Marg: Spines/cm | 1.36 | 0.12 | 0.17 | 0.09 | 0.90 | 0.78 |
| Mid portion Undulation | weak | med-strong | med-weak | medium | weak | weak |
| Rolling | mid-weak | med-weak | med-weak | med strong | weak | med-weak |
| Mature colour | dark green | dark green | dark green | dark green | dark green | dark green |
| RHS Chart No. | 139A | 139A | 139A | 139A | | 137A |
| Immature colour | green | green | green | green | green | green |
| RHS Chart No. | 137B | 137A-B | 141A | 137B | | 143A |
| Margin colour | paler | paler | similar | paler | paler | paler |
| Leaf sheen | medium | med-high | med-high | low | medium | low-med |
| Vein colour | 153 B or C | 152D | 152C | 152D | 153D | |
| | | | FLOWERING AND FRUIT | | | |
| Flowering time | med-late | medium | v-early | early | late | med-late |
| Duration | short | medium | long | | | |
| Nuts/raceme | 1.7 | 1.5 (est) | 2.5 (est) | 2.0 (est) | | 1.5 (est) |

TABLE 1-continued

| Character | HV A4 | Keauhou | Kau | Own Choice | Nutty Glen | Renown |
|---|---|---|---|---|---|---|
| Raceme density on tree | very dense | dense | medium | dense | | med-dense |
| Raceme length | long | short | short-med | medium | long | long |
| Husk color | 137A-B | 137A | 137B | 137A | | 138A |
| Husk thickness | 3.7 mm | 3 mm | 2.7 mm | 3.2 mm | 4.3 mm | 4.4 mm |
| % nut diameter | 14.1% | 11.7% | 10.6% | 12.1% | 15.4% | 16.4% |
| Hilum endpoint | medium | medium | small | med-small | small | large |
| Pedicel shoulder | weak | absent | | absent | absent | weak |
| Dehiscence (1-5) | off-tree 1 | off-tree 1 | off-tree 1 | both 2 | | on-tree 3 |
| Splitting (1-5) | both 3 | off-tree 5 | off-tree 5 | off tree 4 | on-tree 1 | on-tree 2 |
| | | | NUTS | | | |
| Nut Shape | oval | round | round | round | round | oval |
| length/breadth | 1.04 | 0.98 | 0.99 | 1.04 | 0.99 | 1.12 |
| Nut diameter (mm) | 26.27 | 25.55 | 25.00 | 25.96 | 28.04 | 26.85 |
| Range (mm) | 22-30 | 21-30 | 22-28 | 21-30 | 23-34 | 23-30 |
| Std deviation (mm) | 1.38 | 1.46 | 1.37 | 1.57 | 2.02 | 1.45 |
| Kernel weight (gm) | 3.6-3.8 | 2.3-2.7 | 2.2-2.5 | 2.5-2.7 | 4.0 | 3.2-3.6 |
| % of Nut | 43-47 | 34-38 | 32-34 | 33-36 | 46-47 | 39-41 |
| Shell texture | smooth | mild-rough | smooth | smooth | rough | rough |
| Shell sheen | medium | dull | dull | dull | med-shiny | shiny |
| Shell flecking | moderate | slight | moderate | mod-heavy | mod-slight | mod-heavy |
| Micropyle | v-slight | obvious | v-slight | v-slight | v-slight | v-slight |
| Shell colour (dried) | 164A | 165B | 165B | 165A-B | 165A-B | 165B |
| Suture colour | same | same | lighter | same | same | lighter |

We claim:

1. A new and distinct hybrid *Macadamia integrifolia* × *tetraphylla* named Hidden Valley A4 substantially as shown and described.

* * * * *